United States Patent
Gallagher

(10) Patent No.: US 9,877,669 B2
(45) Date of Patent: Jan. 30, 2018

(54) METHOD AND DEVICE FOR MONITORING BODY MOVEMENT BY DETECTING PATTERN CHANGES IN THE DISTANCE VARIATIONS BETWEEN PROXIMITY SENSORS AND THEIR RESPECTIVE SENSOR ZONE

(71) Applicant: Gregory John Gallagher, Cape Town (ZA)

(72) Inventor: Gregory John Gallagher, Cape Town (ZA)

(73) Assignee: SNUZA TRUST, Cape Town (ZA)

( * ) Notice: Subject to any disclaimer, the term of this patent is extended or adjusted under 35 U.S.C. 154(b) by 0 days.

(21) Appl. No.: 14/648,438

(22) PCT Filed: Oct. 15, 2013

(86) PCT No.: PCT/IB2013/059367
§ 371 (c)(1),
(2) Date: May 29, 2015

(87) PCT Pub. No.: WO2014/087266
PCT Pub. Date: Jun. 12, 2014

(65) Prior Publication Data
US 2015/0305653 A1    Oct. 29, 2015

(30) Foreign Application Priority Data
Dec. 6, 2012  (GB) .................... 1221967.1

(51) Int. Cl.
*A61B 5/00* (2006.01)
*A61B 5/08* (2006.01)
*A61B 5/113* (2006.01)

(52) U.S. Cl.
CPC ............ *A61B 5/113* (2013.01); *A61B 5/0816* (2013.01); *A61B 5/4818* (2013.01);
(Continued)

(58) Field of Classification Search
None
See application file for complete search history.

(56) References Cited

U.S. PATENT DOCUMENTS 5,140,992 A * 8/1992 Zuckerwar ......... A61B 5/02411
600/528
6,011,477 A * 1/2000 Teodorescu ............ A61B 5/113
340/573.1
(Continued)

FOREIGN PATENT DOCUMENTS

DE    3109026 A1    9/1982
FR    2571955 A1    4/1986
(Continued)

OTHER PUBLICATIONS

Search Report dated Mar. 25, 2013 in Application GB1221967.1.

*Primary Examiner* — Matthew Kremer
(74) *Attorney, Agent, or Firm* — Polsinelli PC

(57) ABSTRACT

A method and device (10) are provided for monitoring regular movement of the body (20) of a human subject, such as an infant. The device (10) includes electronic circuitry, an alarm and attachment means (14) for attaching to the subject's body (18), a first non-contact proximity sensor (22), and a second proximity sensor. When the device (10) is attached to the subject's body, the two proximity sensors (22,24) monitor movement of the subject's body in two sensor zones a first sensor zone (23) and a second sensor zone (25) that is father from the device than the first sensor zone (23). If a pattern in the distances monitored in either sensor (22,24) changes by a predetermined extent, that alarm is activated.

27 Claims, 1 Drawing Sheet

(52) U.S. Cl.
CPC .......... *A61B 5/6804* (2013.01); *A61B 5/6823* (2013.01); *A61B 5/6838* (2013.01); *A61B 5/6844* (2013.01); *A61B 5/746* (2013.01); *A61B 2503/04* (2013.01); *A61B 2503/12* (2013.01); *A61B 2562/0257* (2013.01)

(56) References Cited

U.S. PATENT DOCUMENTS

| | | | | |
|---|---|---|---|---|
| 2003/0109791 A1* | 6/2003 | Kondo | ................ | A61B 5/021 600/500 |
| 2005/0005935 A1* | 1/2005 | Gradon | ................ | A61B 5/087 128/204.18 |
| 2005/0113703 A1* | 5/2005 | Farringdon | .......... | A61B 5/0428 600/509 |
| 2008/0171945 A1* | 7/2008 | Dotter | ................... | A61B 5/024 600/514 |
| 2008/0183095 A1 | 7/2008 | Austin et al. | | |
| 2009/0088612 A1* | 4/2009 | Bouton | ............... | A61M 1/3653 600/309 |
| 2010/0094102 A1* | 4/2010 | Zhang | ................. | A61B 5/0008 600/301 |
| 2010/0201524 A1* | 8/2010 | Gallagher | ............. | A61B 5/113 340/573.1 |
| 2010/0241018 A1 | 9/2010 | Vogel | | |
| 2010/0328075 A1* | 12/2010 | Rahamim | ............ | A61B 5/1135 340/573.1 |
| 2011/0032103 A1* | 2/2011 | Bhat | .................... | G08B 13/196 340/573.1 |
| 2011/0060215 A1 | 3/2011 | Tupin, Jr. et al. | | |
| 2011/0112793 A1 | 5/2011 | Diebold et al. | | |

FOREIGN PATENT DOCUMENTS

| | | |
|---|---|---|
| WO | WO-01/76467 A2 | 10/2001 |
| WO | WO-2008/096328 A2 | 8/2008 |
| WO | WO-2009/050702 A2 | 4/2009 |
| WO | WO-2011/054548 A1 | 5/2011 |
| WO | WO-2011/073823 A1 | 6/2011 |

* cited by examiner

METHOD AND DEVICE FOR MONITORING BODY MOVEMENT BY DETECTING PATTERN CHANGES IN THE DISTANCE VARIATIONS BETWEEN PROXIMITY SENSORS AND THEIR RESPECTIVE SENSOR ZONE

CROSS REFERENCE TO RELATED APPLICATIONS

This application is a National Phase filing under 35 U.S.C. § 371 of PCT/IB2013/059367 filed on Oct. 15, 2013; and this application claims priority to Application No. 1221967.1 filed in United Kingdom on Dec. 6, 2012. The entire contents of each application are hereby incorporated by reference.

FIELD OF THE INVENTION

This invention relates to monitoring movements of the human body by way of apparatus worn on the person. The invention is useful in monitoring breathing and/or other movement of infants, but can also be used on adults, e.g. patients who are prone to respiratory disruptions while asleep.

BACKGROUND TO THE INVENTION

Various breathing or apnoea monitors have been developed that are intended to be worn by infants and one of the monitors that is most reliable is described in WO 2008/096328 and is sold commercially under the name SNUZA®.

The present invention seeks to enhance the reliability, comfort and/or versatility of human motion monitors.

SUMMARY OF THE INVENTION

According to one aspect of the present invention there is provided a device for monitoring regular movement of the body of a human subject such as an infant, said device comprising:
  electronic circuitry including at least one alarm;
  attachment means for releasably attaching the device to the subject's body; and
  at least one first proximity sensor that is a non-contact proximity sensor and that is configured to monitor a distance between the device and a near object in a first sensor zone,
  wherein said device includes at least one second proximity sensor that is a non-contact proximity sensor and that is configured to monitor a distance between the device and a near object in a second sensor zone;
  said attachment means and said first and second proximity sensors being configured such that the second sensor zone is disposed farther from the attachment means than the first sensor zone; and
  said circuitry being configured to activate the alarm in the event that a pattern by which the distance measured by at least one of the first proximity sensor and the second proximity sensor varies, changes to a predetermined extent.

Referring to the presence in the device of a "first" proximity sensor and a "second" proximity sensor, does not imply that these are the only two sensors in the device. There may be any number of additional sensors in the device and some of them may duplicate the "first" and "second" sensor.

The first and second sensor zones may extend from the device towards the body of the subject, when the device is attached to an article of clothing of the subject and the first and second proximity sensors may be directed to detect the distances between the device and the stomach of the subject in the first and second sensor zones, respectively, when the device is attached to an article of clothing in the subject's groin area.

The term "groin" refers herein to the area that is typically covered by the waistband of a diaper and that is generally in the pelvic or pubic area. The term "stomach" refers to the exterior of the lower abdominal region, corresponding generally to the position of the internal organ by the same name.

The attachment means may include a clip, preferably a protruding clip, that is attachable to the article of clothing and the first sensor zone and the second sensor zone may extend on the same side of the device, to which the clip protrudes.

The device may include a third proximity sensor that is a non-contact proximity sensor and that is configured to monitor the distance between the device and a near object in a third sensor zone, said third sensor zone extending in a direction from the device, generally opposite from the direction in which at least one of the first and second sensor zones extend.

The device may include an accelerometer that is connected to the electronic circuitry of the device.

According to another aspect of the present invention there is provided a method of monitoring regular movement of the body of a human subject such as an infant, said method including:
  releasably attaching a monitoring device to the subject's body; and
  directing at least one first proximity sensor from the device to the body of the subject, to monitor movement of the subjects body in a first sensor zone;
  characterised by directing at least one second proximity sensor from the monitoring device to the subject's body to monitor movement of the subject's body in a second sensor zone, said second sensor zone being disposed farther from the attachment of the monitoring device to the subject's body, than the first sensor zone;
  detecting regular movement of the subject's body relative to the monitoring device by monitoring the distance between said body and the first and second proximity sensors in the first and second sensor zones, respectively; and
  activating an alarm if a pattern of said monitored distance changes to a predetermined extent in at least one of the first and second sensing zones.

The method may include attaching the device to the subject's body in the groin area, directing the first and second proximity sensors to the body in the stomach area, and detecting regular movement of the stomach relative to the monitoring device by monitoring the distance between the stomach and the monitoring device in the first sensor zone and the second sensor zone.

The method may include attaching the device to an article of clothing worn by the subject, such as a diaper.

The method may include selecting one of the distance between the subject's body and the first proximity sensor or the distance between the subject's body and the second proximity sensor, whichever distance varies with the greatest amplitude, and activating said alarm if the pattern of said selected distance changes to a predetermined extent.

The change in the pattern of the monitored distance may be that the interval between successive increases or decreases in the distance, exceeds a predetermined maximum period or is shorter than a predetermined minimum period.

The method may include detecting the presence of objects in a third sensor zone, said third sensor zone extending away from said subject's body, and activating the alarm if an object is detected in the third sensor zone. The method may include monitoring the distance between the device and said object in the third sensor zone and activating the alarm only if said distance deviates to a predetermined extent from the pattern of the distance measured by at least one of the first proximity sensor and the second proximity sensor.

The method may include detecting movement of the device, e.g. by detecting acceleration or orientation of the device, and disregarding changes in the pattern of the monitored distance, caused by movement of the device.

BRIEF DESCRIPTION OF THE DRAWINGS

For a better understanding of the present invention, and to show how the same may be carried into effect, reference will now be made, by way of non-limiting example, to the accompanying drawings, in which:

FIG. 1 shows a diagrammatic side view of a monitoring device in accordance with the present invention, fitted on a waistband of an infant's diaper that is tight fitting; and.

DETAILED DESCRIPTION OF THE DRAWINGS

Figure 1:
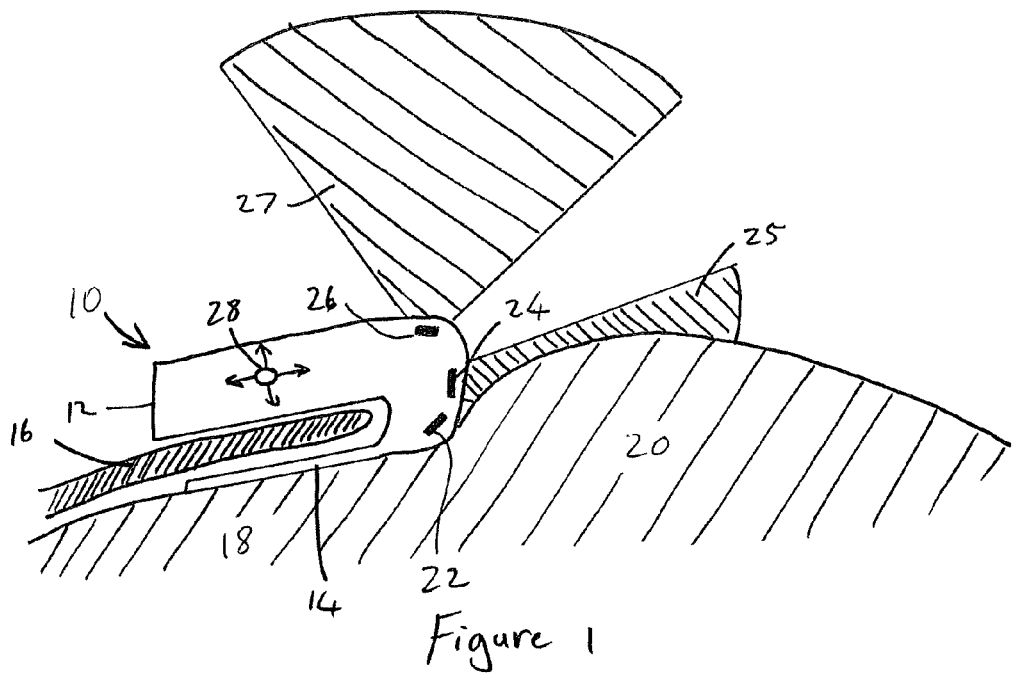

Referring to the drawings, a monitoring device in accordance with the present invention is generally indicated by reference numeral 10.

The device 10 includes a casing 12 that houses electronic circuitry, a power source and alarms. The casing 12 includes an external clip 14 by which it is attachable to a garment such as a diaper 16 (e.g. at the upper edge or waistband of a diaper) in the groin area 18 of a wearer of the device. These features of the device 10 are generally similar to their counterparts described in WO 2008/096328.

Unlike the monitors described in WO 2008/096328, the device 10 of the present invention does not include a protuberance that extends from the casing 12. Instead, the device 10 includes two or more, preferably three, distance or proximity sensors that are housed in the casing 12.

The first proximity sensor 22 is directed generally towards the body of the wearer, i.e. it is directed to the same side of the device 10, as that on which the clip 14 is provided. The first sensor zone in which first sensor 22 can detect the proximity of objects, is identified by reference number 23 in FIG. 2 and lies adjacent the device 10 in the stomach area 20.

The second proximity sensor 24 is also directed generally towards the body of the wearer to the same side of the device 10, as that on which the clip 14 is provided and the second sensor zone in which second sensor 24 can detect the proximity of objects, is identified by reference number 25 in the drawings. However, unlike the first sensor zone 23 that lies adjacent the device 10, the second sensor zone 25 lies further from the device 10 in the stomach area 20. In the illustrated embodiment, the first and second sensor zones 23 and 25 do not overlap, but this is not essential.

The third proximity sensor 26 is directed generally away from the body of the wearer, i.e. to a side of the device 10 that is opposite from that on which the clip 14 is provided.

The third sensor zone in which the third sensor 26 can detect the proximity of objects, is identified by reference number 27 in the drawings. In the illustrated embodiment, the second and third sensor zones 25 and 27 do not overlap, but this is not essential.

The sensors 22,24,26 are non-contact type sensors that measure the distance or proximity between the sensor and a nearby object in the sensor zone 23,25,27. Suitable sensors 22,24,26 include optical or infrared sensors and capacitive sensors.

The first and second sensors 22,24 and the internal electronic circuitry of the device 10 are configured to detect the distances between the first and second sensors 22,24, respectively, and the stomach 20 of the wearer continually (continuously or at short, regular intervals) and to signal these detected distances to a processor or CPU of the electronic circuitry. Likewise, the third sensor 26 and the internal electronic circuitry of the device 10 are configured to detect the distance between the third sensor an any object that may be present in the third sensor zone 27, continually, and to signal the presence of such and object and/or the detected distance to the processor or CPU.

In use, when the movement of a human subject such as the infant needs to be monitored in order to be alerted to apnoea, abnormal breathing, or the like, the device 10 is releasably attached to the body of the subject (wearer) by clipping it to the diaper waistband 16, or like article of clothing, with the clip 14 extending underneath the diaper and with the first and second sensors 22,24 directed to the wearer's stomach 20.

The positions of a diaper waistband 16, groin 18 and stomach 20 are not exactly defined or consistent between different wearers, but it has been found, particularly with infants, that the groin area 18 moves relatively little during breathing, compared to the stomach 20 (which expands and contracts markedly). Accordingly, as the wearer breathes, there is fairly regular relative movement between the more stable groin area 18 and the stomach 20.

The tightness with which the diaper waistband 16 (or analogous article of clothing) extends around the wearer's body can vary—especially in the case of small infants, because of the difficulty of fitting diapers on such small bodies, the softness of their bodies and often because of inexperience of their caregivers.

If the device 10 is fitted on a waistband 16 of a diaper that is tight fitting, the device—more particularly, the clip 14, will be pressed tightly against the groin area 18 and the wearer's body may bulge adjacent the top of the device in the stomach area 20, as shown somewhat exaggerated in FIG. 1. In this case, the wearer's body may be immediately adjacent the device 10 in the region of the first sensor 22 and there will be no regular movement of the body in the first sensor zone 23 that can be detected by the first sensor. However, the wearer's stomach 20 will still protrude into the second sensor zone 25 and its regular movement can be detected by the second sensor 24.

Figure 2:
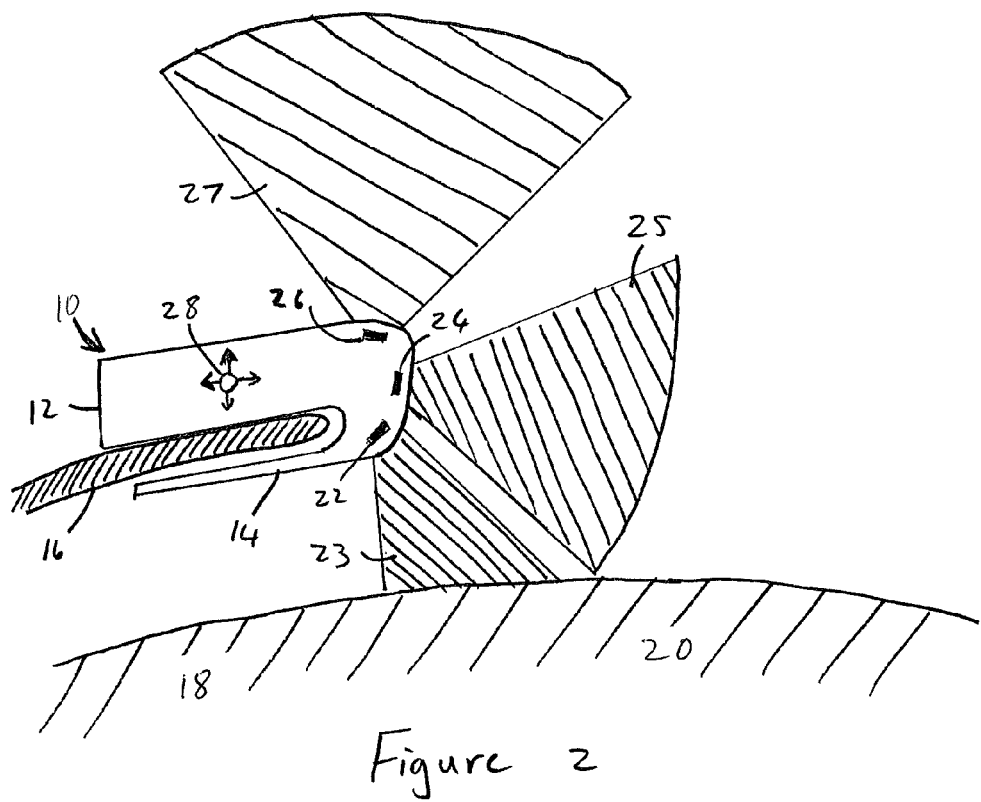
FIG. 2 shows a diagrammatic side view of the monitoring device and waistband of FIG. 1, where the diaper is loose fitting

If the device 10 is fitted on a waistband 16 of a diaper that is loose fitting, the device may be spaced away from the groin area 18 as shown somewhat exaggerated in FIG. 2. In this case, the wearer's body may be spaced too far from the second sensor 24 and may not fall within the second sensor zone 25, so that no regular movement of the body in the second sensor zone 25 that can be detected by the second sensor. However, the wearer's stomach will still protrude into the first sensor zone 23 without being pressed against the device 10, so that it can more freely relative to the device 10 and its regular movement in the first sensor zone 23 can be detected by the first sensor 22.

If the device 10 is fitted on a waistband 16 of a diaper with a tightness of fit somewhere between the two extremes illustrated in FIGS. 1 and 2, the extent to which the wearer's stomach 20 extends into the first and second sensor zones 23 and 25, the extent to which the stomach is spaced from the device 10 in the first and second sensor zones, and the extent to which regular movement of the stomach can be detected in the first and second sensor zones, will vary. However, since the second sensor zone 25 is spaced farther from the device 10 than the first sensor zone 23, the regular stomach movement will always be detectable in at least one of the first and second sensor zones.

The circuitry inside the casing 12 is configured to monitor variations in the distances between the device 10 and the wearer's stomach 20 in the first and second sensor zones 23,25, as detected by the first and second sensors 22,24, as an indication of breathing movements. Preferably, the circuitry is configured to compare the amplitude variations between signals received from the first and second sensors 22,24 and to select one of these signals temporarily for assessment of the wearer's breathing movements. The selection between signals received from the first and second sensors 22,24 can be repeated from time to time and can be based features of the signals instead of or in addition to a comparison between the signals' amplitudes, e.g. either of the signals may be temporarily selected for assessment of the wearer's breathing movement if it is becomes difficult to detect regular variation in the signal of the other sensor.

The circuitry is configured to activate one or more of the alarms in the device 10, if the detected regular distance variation (as detected by the first or second sensor 22,24—whichever is temporarily selected) in either of the first and second sensor zones 23,25, deviates from a pattern by a predetermined extent. The options of configurations of the circuitry to determine when an alarm needs to be activated are unlimited, but it can be configured to activate the alarm when the period between consecutive variations in the distance detected by the first or second sensor 22,24 is longer than a predetermined time (possibly caused by apnoea) or is too short (possibly caused by hyperventilation or suffocation). Further, the circuitry can be configured with a degree of intelligence to anticipate the respiratory rhythm of a particular wearer, to filter out or ignore anomalies when the wearer sighs, yawns, or the like, without activating the alarm.

The third sensor 26 is not intended to detect regular breathing movements of the wearer's stomach, but is instead intended to detect the presence of and distance to objects or bodies in the third sensor zone 27 that may pose a threat to the wearer, such as co-sleeping siblings, pets, toys, or the like. The third sensor 26 could also detect the presence of a bed, or the like, if the wearer changes from a desired sleeping position (e.g. rolls over from lying on his back)—particularly if a very young wearer rolls onto his stomach.

The circuitry is configured to activate one or more of the alarms in the device 10, if the third sensor 26 detects the presence of an object in the third sensor zone 27, but in order to avoid raising false alarms if the objects detected are part of the subject's anatomy (particularly the subject's arms or hands), the alarm is only activated in the event that the distance detected by the third sensor 26 (i.e. the distance between the device 10 and the detected object) deviates to a predetermined extent from the pattern of the regular distance variation detected by the first or second sensor 22,24—whichever is temporarily selected. Accordingly, if the distance measured by the third sensor 26 generally changes in phase and with the same frequency of the regular breathing movements of the subject's stomach 20, then it is assumed that the object detected in the third sensor zone 27 is part of the subject's anatomy and the alarm is not raised.

Any one or more of the first, second or third sensors 22,24,26 are preferably duplicated to improve performance of the device 10.

In a preferred embodiment, the device 10 also includes an accelerometer 28 attached to or housed inside the casing 12. The accelerometer 28 can detect movement of the wearer, e.g. when the wearer rolls over or moves in any other way and this information is also sent by signal to the CPU of the device. In the CPU, the motion detected by the accelerometer 24 and the motion detected by the first and second sensors 22,24 are compared to assess whether disturbances in the breathing patterns detected by the sensors 22,24 may have been caused by other body movements (detected by the accelerometer 28)—in which case the alarm would not be activated.

The accelerometer 28 and electronic circuitry can also be configured to activate the alarm if the wearer changes physical orientation—e.g. if a very young wearer changes from a desired sleeping position (e.g. rolls over from lying on his back).

The invention claimed is:

1. A device for monitoring movement of a body of a human subject, said device comprising:
    electronic circuitry including at least one alarm;
    a connector for releasably attaching the device to the subject's body in a groin area of said subject's body; and
    at least one first proximity sensor,
    wherein said first proximity sensor is configured and directed to measure a distance between the device and a part of a stomach of the subject that is in a first sensor zone, when the device is attached to the subject's body in the groin area;
    and wherein said device includes at least one second proximity sensor that is configured and directed to measure a distance between the device and a part of the stomach of the subject that is in a second sensor zone, when the device is attached to the subject's body in the groin area;
    said connector and said first proximity sensor and said second proximity sensor being configured such that the second sensor zone is disposed farther from the connector than the first sensor zone; and
    said circuitry being configured to activate the alarm if a pattern by which the distance measured by at least one of the first proximity sensor and the second proximity sensor varies, changes to a predetermined extent;
    wherein the device is a one-piece unit, and wherein said first proximity sensor and second proximity sensor are configured such that when the device is attached to the subject's body, a bottom of the second sensor zone is above the device along the stomach, and a top of the second sensor zone is above a top of the first sensor zone along the stomach.

2. The device according to claim 1, wherein the connector is configured to attach the device to an article of clothing of the subject.

3. The device according to claim 2, wherein the connector includes a clip that is attachable to the article of clothing.

4. The device according to claim 3, wherein the first sensor zone and the second sensor zone extend on a side of the device, to which the clip protrudes.

5. The device according to claim 4, wherein said device includes a third proximity sensor that is configured to monitor a third distance between the device and an object in a third sensor zone, said third sensor zone extending in a direction from the device, that is opposite from a direction in which at least one of the first and second sensor zones extend.

6. The device according to claim 3, wherein said device includes a third proximity sensor that is configured to monitor a third distance between the device and an object in a third sensor zone, said third sensor zone extending in a direction from the device, that is opposite from a direction in which at least one of the first and second sensor zones extend.

7. The device according to claim 2, wherein said device includes a third proximity sensor that is configured to monitor a third distance between the device and an object in a third sensor zone, said third sensor zone extending in a direction from the device, that is opposite from a direction in which at least one of the first and second sensor zones extend.

8. The device according to claim 1, wherein said device includes a third proximity sensor that is configured to monitor a third distance between the device and an object in a third sensor zone, said third sensor zone extending in a direction from the device, that is opposite from a direction in which at least one of the first and second sensor zones extend.

9. A method of monitoring movement of a body of a human subject said method comprising:
   releasably attaching a monitoring device to the subject's body in a groin area;
   directing at least one first proximity sensor from the device to a stomach of the subject, to measure movement of the subject's stomach in a first sensor zone;
   directing at least one second proximity sensor from the monitoring device to the subject's stomach to measure movement of the subject's stomach in a second sensor zone, said second sensor zone being disposed farther from the attachment of the monitoring device to the subject's body in the groin area, than the first sensor zone;
   measuring movement of the subject's stomach relative to the monitoring device by measuring a first distance between said stomach and the first proximity sensor in the first sensor zone and measuring a second distance between said stomach and the second proximity sensor in the second sensor zone; and
   activating an alarm if a pattern of at least one of said first distance and said second distance changes to a predetermined extent.

10. The method according to claim 9, wherein the releasably attaching includes attaching the device to an article of clothing worn by the subject.

11. The method according to claim 10, which comprises selecting one of the first distance or the second distance, by determining an amplitude by which each of said first and second distances varies and selecting a distance from the first and second distances with the greatest amplitude, and activating the alarm if the pattern of said selected distance changes to the predetermined extent.

12. The method according to claim 11, wherein said change in the pattern of the selected distance, is that a period between successive increases or decreases in the selected distance, exceeds a predetermined maximum period.

13. The method according to claim 11, wherein said change in the pattern of the selected distance, is that a period between successive increases or decreases in the selected distance, is shorter than a predetermined minimum period.

14. The method according to claim 11, which includes monitoring a third sensor zone, said third sensor zone extending away from said subject's body, and activating an alarm if an object is detected in the third sensor zone.

15. The method according to claim 10, wherein said change in the pattern of the at least one of the first distance and the second distance, is that a period between successive increases or decreases in the first distance or the second distance, exceeds a predetermined maximum period.

16. The method according to claim 10, which comprises monitoring a third sensor zone, said third sensor zone extending away from said subject's body, and activating an alarm if an object is detected in the third sensor zone.

17. The method according to claim 16, which comprises monitoring a third distance between the device and said object in the third sensor zone and activating the alarm in response to a pattern in said third distance deviating to a predetermined extent from the pattern of the at least one of the first distance and the second distance.

18. The method according to claim 9, which comprises selecting one of the first distance or the second distance, by determining an amplitude by which each of said first and second distances varies and selecting a distance from the first and second distances with the greatest amplitude, and activating the alarm if the pattern of said selected distance changes to the predetermined extent.

19. The method according to claim 18, wherein said change in the pattern of the selected distance, is that a period between successive increases or decreases in the selected distance, exceeds a predetermined maximum period.

20. The method according to claim 18, wherein said change in the pattern of the selected distance, is that a period between successive increases or decreases in the selected distance, is shorter than a predetermined minimum period.

21. The method according to claim 18, which includes monitoring third sensor zone, said third sensor zone extending away from said subject's body, and activating the alarm if an object is detected in the third sensor zone.

22. The method according to claim 21, which includes monitoring a third distance between the device and said object in the third sensor zone and activating the alarm in response to a pattern in said third distance deviating to a predetermined extent from the pattern of the at least one of the first distance and the second distance.

23. The method according to claim 9, wherein said change in the pattern of the at least one of the first distance and the second distance, is that a period between successive increases or decreases in the at least one of the first distance and the second distance, exceeds a predetermined maximum period.

24. The method according to claim 9, wherein said change in the pattern of the at least one of the first distance and the second distance, is that a period between successive increases or decreases in the at least one of the first distance and the second distance, is shorter than a predetermined minimum period.

25. The method according to claim 9, which includes monitoring a third sensor zone, said third sensor zone extending away from said subject's body, and activating the alarm if an object is detected in the third sensor zone.

26. The method according to claim 25, which comprises monitoring a third distance between the device and said object in the third sensor zone and activating the alarm in response to a pattern in said third distance deviating to a predetermined extent from the pattern of at least one of the first distance and the second distance.

27. The method according to claim 9, wherein the device is a one-piece unit, and wherein said directing at least one second proximity sensor defines the second sensor zone such that a bottom of the second sensor zone is above the device along the stomach, and a top of the second sensor zone is above a top of the first sensor zone along the stomach.

\* \* \* \* \*